United States Patent [19]

Horwell et al.

[11] 4,277,480
[45] Jul. 7, 1981

[54] TETRAHYDROINDOLOISOQUINOLINES

[75] Inventors: David C. Horwell, Farnborough; David E. Tupper, Bracknell, both of England

[73] Assignee: Lilly Industries Limited, London, England

[21] Appl. No.: 141,752

[22] Filed: Apr. 18, 1980

Related U.S. Application Data

[63] Continuation of Ser. No. 39,076, May 14, 1979, abandoned.

[30] Foreign Application Priority Data

May 23, 1978 [GB] United Kingdom ............ 21355/78
Apr. 12, 1979 [GB] United Kingdom ............ 1200/79

[51] Int. Cl.³ ............... C07D 487/06; A61K 31/475
[52] U.S. Cl. ............................ 424/258; 546/67; 546/61
[58] Field of Search ............... 546/67, 69; 424/258

Primary Examiner—Mary C. Lee
Attorney, Agent, or Firm—James L. Rowe; Arthur R. Whale

[57] ABSTRACT

Isoquinoline compounds of the following formula are described:

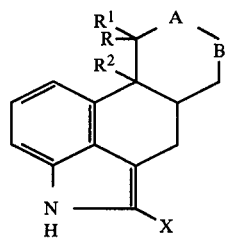

wherein the moiety A-B represents a group of formula;

$-CH_2-NR^3-$ or $-NR^3-CH_2-$;

wherein $R^3$ represents hydrogen, $C_{1-6}$ alkyl, $C_{3-6}$ cycloalkyl, $C_{3-6}$ cycloalkyl $C_{1-4}$ alkyl, optionally substituted benzyl, $C_{3-6}$ alkenyl or $C_{1-4}$ alkanoyl;
wherein R represents hydrogen, $C_{1-6}$ alkyl, $C_{3-6}$ cycloalkyl, or optionally substituted benzyl;
wherein $R^1$ and $R^2$ each represent hydrogen or taken together represent a chemical bond; and wherein X is hydrogen or halogen; or an acid-addition salt thereof.

The compounds are pharmaceuticals and especially useful in the treatment of disorders of the central nervous system.

9 Claims, No Drawings

TETRAHYDROINDOLOISOQUINOLINES

This is a continuation of application Ser. No. 39,076, filed May 14, 1979, now abandoned.

This invention relates to novel heterocyclic derivatives possessing a wide variety of pharmacological effects, to pharmaceutical formulations containing the novel derivatives, to processes of preparation thereof and to methods of treating or preventing disorders of the central nervous system in animals including humans by treatment therewith.

Compounds based on the ergoline ring system:

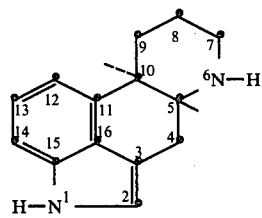

have a surprising variety of pharmaceutical activities. For example, the amides of lysergic acid have valuable and unique pharmacological properties, and include the naturally occurring peptide alkaloids; ergocornine, ergokryptine, ergonovine, ergocristine, ergosine, and ergotamine, synthetic oxytocic alkaloids such as methergine, and the synthetic hallucinogenlysergic acid diethylamide or LSD. Ergotamine, a 9-ergolene, with a peptide side chain, has been used in the treatment of migraine and recently, both ergocornine and 2-bromo-α-ergokryptine have been shown to be inhibitors of prolactin and of dimethylbenzanthracene-induced tumors in rats, according to Nagasawa and Meites, *Proc. Soc. Exp'tl. Bio. Med.* 135, 469 (1970) and to Heuson et al., *Europ. J. Cancer,* 353 (1970) and see also U.S. Patent Specifications Nos. 3,752,888 and 3,752,814. Non-peptide ergot derivatives, both naturally occurring and totally or partially synthetic, share these multiple pharmacological properties with the peptide derivatives. For example, D-6-methyl-8-cyanomethylergoline was prepared by Semonsky and coworkers, *Coll. Czech. Chem. Commun.,* 33, 577 (1968), and was found to be useful in preventing pregnancy in rats—*Nature,* 221, 666 (1969) and see also U.S. Pat. No. 3,732,231—by interfering with the secretion of hypophysial leuteotropic hormone and the hypophysial gonadotropins or by inhibiting the secretion of prolactin (see Seda et al., *Reprod. Fert.,* 24, 263 (1971) and Mantle and Finn, id. 441). Semonsky and coworkers, *Coll. Czech. Chem. Comm.,* 36, 220 (1971), have also prepared D-6-methyl-8-ergolinylacetamide, a compound which is stated to have anti-fertility and anti-lactating effects in rats. The 2-halo derivatives of D-6-methyl-8-cyanomethylergoline and of D-6-methyl-8-ergolinylacetamide have been prepared and tested for their prolactin inhibiting activity (M. J. Sweeney, J. A. Clemens, E. C. Kornfeld and G. A. Poore, 64th Annual Meeting *Amer. Assoc. Cancer Research,* April, 1973). However, heretofore no attempt has been made to prepare 7- or 8-aza analogues of the 6-aza naturally occurring ergot derivatives described above.

An object of the present invention is to provide novel isoquinoline derivatives having valuable pharmacological properties.

Accordingly, in one aspect of the invention there is provided an isoquinoline of formula (I):

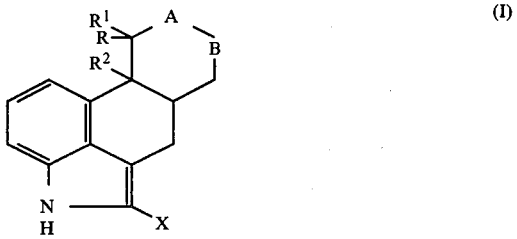

wherein the moiety A-B represents a group of formula:

—$CH_2$—$NR^3$— or —$NR^3$—$CH_2$—;

wherein $R^3$ represents hydrogen, $C_{1-6}$ alkyl, $C_{3-6}$ cycloalkyl, C-3-6 cycloalkyl $C_{1-4}$ alkyl, optionally substituted benzyl, $C_{3-6}$ alkenyl or $C_{1-4}$ alkanoyl;

wherein R represents hydrogen, $C_{1-6}$ alkyl, $C_{3-6}$ cycloalkyl or optionally substituted benzyl;

wherein $R^1$ and $R^2$ each represent hydrogen or taken together represent a chemical bond; and wherein X is hydrogen or halogen; or an acid-addition salt thereof.

When A-B represents a group of formula —$CH_2$—$NR^3$—, the compounds of formula (I) may be represented by the structure (II):

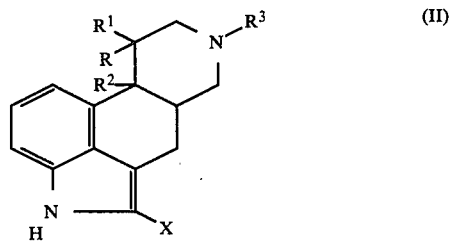

When A-B represents a group of formula —$NR^3$—$CH_2$—, the compounds of formula (I) may be represented by the structure (III):

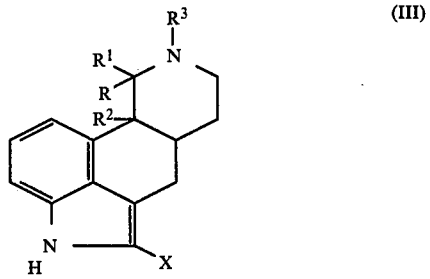

For such compounds it is preferred that $R^1$ and $R^2$ are each hydrogen The term $C_{1-6}$ alkyl includes both branched and straight chain groups, such as for example, methyl, ethyl, n-propyl, isopropyl, n-butyl, sec-butyl, t-butyl, n-pentyl and n-hexyl. Reference to $C_{3-6}$ cycloalkyl means cyclopropyl, cyclobutyl, cyclopentyl and cyclohexyl and $C_{3-6}$ cycloalkyl $C_{1-4}$ alkyl includes groups such as those defined as $C_{3-6}$ cycloalkyl linked to an alkyl group such as those listed above containing 1 to 4 carbon atoms. The benzyl group is preferably unsubstituted but substitution includes for example 1 to 3 substituents such as halogen, alkyl especially methyl, alkoxy especially methoxy, and nitro. The term $C_{3-6}$ alkenyl includes, for example, the radicals allyl and 3,3-dimethylpropen-2-yl and the term $C_{1-4}$ alkanoyl includes for example, acetyl and propanoyl. Halogen includes fluorine, chlorine, bromine and iodine, and is most preferably chlorine and bromine.

In the case of both formulae II and III above, it is preferred that R and/or $R^3$ should be $C_{1-4}$ alkyl groups especially methyl and X is hydrogen. A further preferred group is one in which X is chlorine or bromine.

Illustrative examples of novel isoquinolines in accordance with the invention are listed below:

1,4,5,6,7,8-hexahydroindolo[4,3-fg]isoquinoline;
7-methyl-1,4,5,6,7,8-hexahydroindolo[4,3-fg]isoquinoline;
7,9-dimethyl-1,4,5,6,7,8-hexahydroindolo[4,3-fg]isoquinoline;
7-n-propyl-9-methyl-1,4,5,6,7,8-hexahydroindolo[4,3-fg]isoquinoline;
7-n-hexyl-9-methyl-1,4,5,6,7,8-hexahydroindolo[4,3-fg]isoquinoline;
7-isopropyl-9-methyl-1,4,5,6,7,8-hexahydroindolo[4,3-fg]isoquinoline;
7-cyclopropyl-9-methyl-1,4,5,6,7,8-hexahydroindolo[4,3-fg]isoquinoline;
7-cyclopropylmethyl-9-methyl-1,4,5,6,7,8-hexahydroindolo[4,3-fg]isoquinoline;
7-benzyl-1,4,5,6,7,8-hexahydroindolo[4,3-fg]isoquinoline;
7-allyl-9-methyl-1,4,5,6,7,8-hexahydroindolo[4,3-fg]isoquinoline;
7-(3,3-dimethylpropen-2-yl)-9-methyl-1,4,5,6,7,8-hexahydroindolo[4,3-fg]isoquinoline;
7-acetyl-9-methyl-1,4,5,6,7,8-hexahydroindolo[4,3-fg]isoquinoline;
9-methyl-1,4,5,6,7,8-hexahydroindolo[4,3-fg]isoquinoline;
9-ethyl-1,4,5,6,7,8-hexahydroindolo[4,3-fg]isoquinoline;
9-ethyl-7-methyl-1,4,5,6,7,8-hexahydroindolo[4,3-fg]isoquinoline;
9-benzyl-7-methyl-1,4,5,6,7,8-hexahydroindolo[4,3-fg]isoquinoline;
9-methyl-1,4,5,6,7,8,9,10-octahydroindolo[3,4-gh]isoquinoline;
8,9-dimethyl-1,4,5,6,7,8,9,10-octahydroindolo[3,4-gh]isoquinoline;
8-n-propyl-9-methyl-1,4,5,6,7,8,9,10-octahydroindolo[3,4-gh]isoquinoline;
8-n-hexyl-9-methyl-1,4,5,6,7,8,9,10-octahydroindolo[3,4-gh]isoquinoline;
8-isopropyl-9-methyl-1,4,5,6,7,8,9,10-octahydroindolo[3,4-gh]isoquinoline;
8-cyclopropyl-9-methyl-1,4,5,6,7,8,9,10-octahydroindolo[3,4-gh]isoquinoline;
8-cyclopropylmethyl-9-methyl-1,4,5,6,7,8,9,10-octahydroindolo[3,4-gh]isoquinoline;
8-benzyl-9-methyl-1,4,5,6,7,8,9,10-octahydroindolo[3,4-gh]isoquinoline;
8-allyl-9-methyl-1,4,5,6,7,8,9,10-octahydroindolo[3,4-gh]isoquinoline;
8-(3,3-dimethylpropen-2-yl)-9-methyl-1,4,5,6,7,8,9,10-octahydroindolo[3,4-gh]isoquinoline; and
8-acetyl-9-methyl-1,4,5,6,7,8,9,10-octahydroindolo[3,4-gh]isoquinoline;
2-bromo-7,9-dimethyl-1,4,5,6,7,8-hexahydroindolo[4,3-fg]isoquinoline;
2-chloro-7-methyl-1,4,5,6,7,8-hexahydroindolo[4,3-fg]isoquinoline;
2-bromo-7-cyclopropylmethyl-9-methyl-1,4,5,6,7,8-hexahydroindolo[4,3-fg]isoquinoline;
2-bromo-8,9-dimethyl-1,4,5,6,7,8,9,10-octahydroindolo[3,4-gh]isoquinoline
2-chloro-9-methyl-1,4,5,6,7,8,9,10-octahydroindolo[3,4-gh]isoquinoline
2-bromo-8-cyclopropylmethyl-9-methyl-1,4,5,6,7,8,10-octahydroindolo[3,4-gh]isoquinoline The novel isoquinolines of the invention are useful both in their free base and acid addition salt forms. The acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicylic, o-acetoxybenzoic, nicotinic or isonicotinic acid, or organic sulphonic acids for example methane sulphonic, ethane sulphonic, 2-hydroxyethane sulphonic, toluene-p-sulphonic, or naphthalene-2-sulphonic acid. Apart from pharmaceutically acceptable acid addition salts, other salts are also included within the scope of acid addition salts such as, for example, those with picric or oxalic acid; they may serve as intermediates in the purification of the compounds or in the preparation of other, for example, pharmaceutically acceptable, acid addition salts, or are useful for identification, characterization or purification of the bases.

The compounds of the invention can be prepared from the ketone of formula (IV):

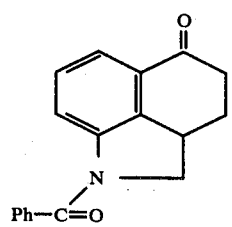
(IV)

described, for example, by Kornfeld et al in the *Journal of the American Chemical Society*, 78, 3087 (1956) using the following reaction schemes:

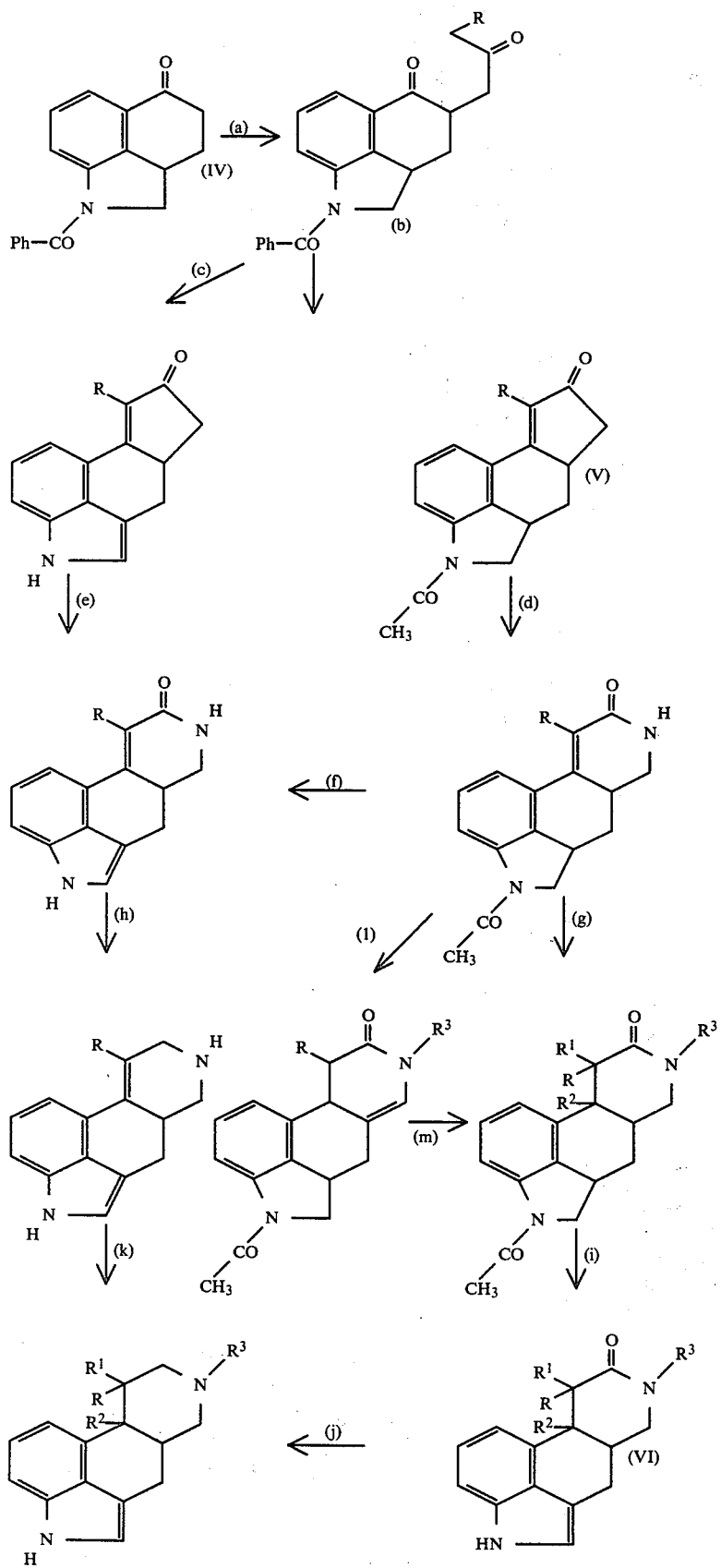

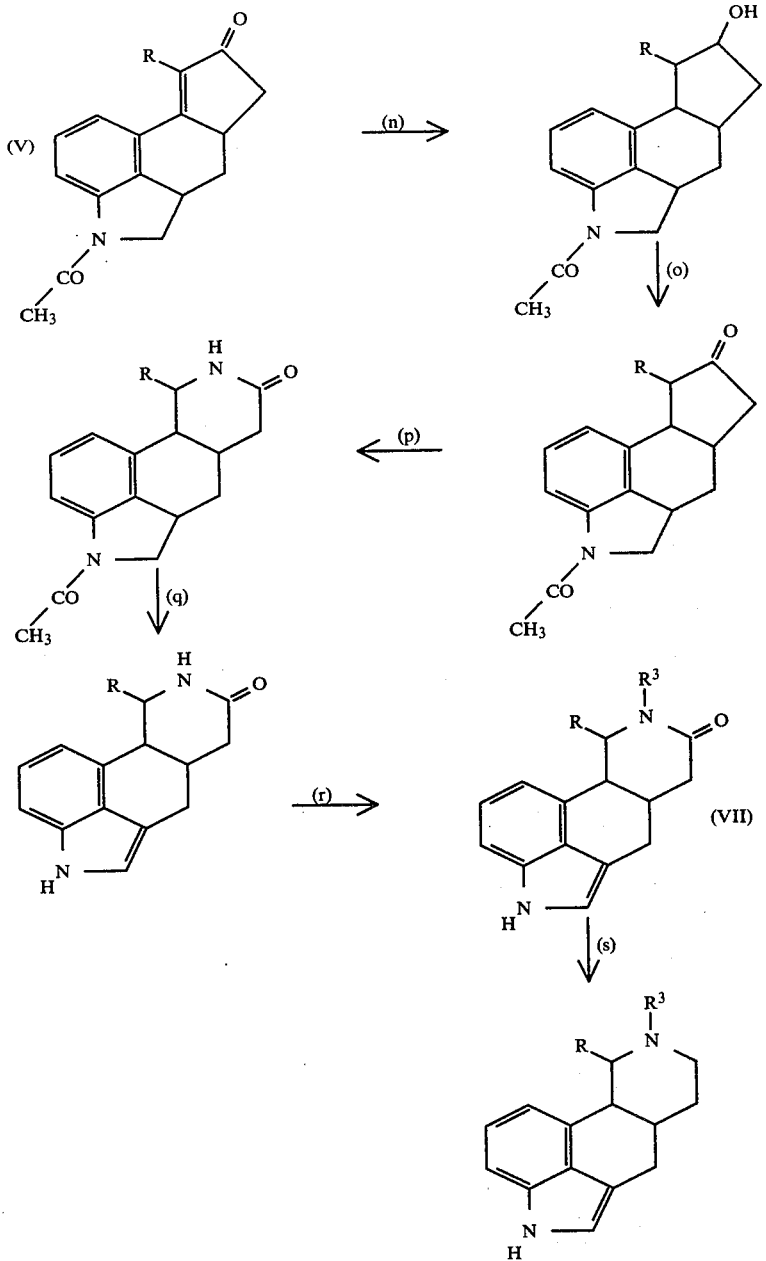

Reaction (a) can be effected by forming the corresponding enolate with lithium diisopropylamide in any suitable inert organic solvent such as tetrahydrofuran at temperatures between −70° C. and 0° C., followed by alkylation with any suitable acetonylating agent such as a 2-nitroalkene, for example 2-nitropropene, after which alkylation, hydrolysis with a strong acid for example perchloric acid gives the diketone.

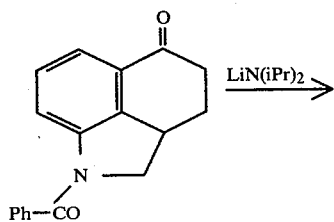

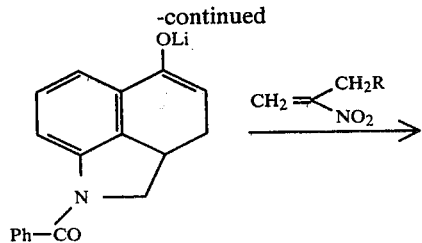

-continued

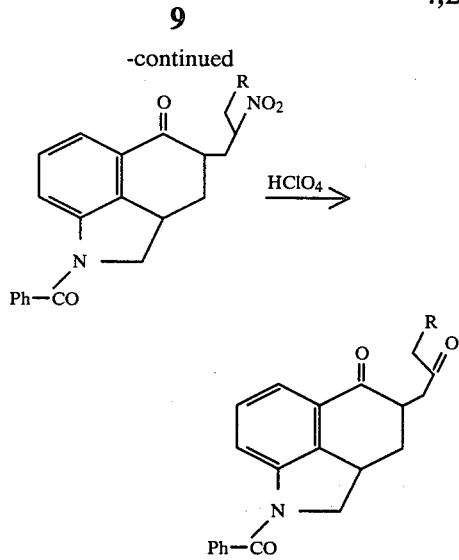

The cyclisation step (b) is an aldol condensation which can be effected by refluxing the diketone with a strong base such as potassium hydroxide in an alkanoic solvent such as ethanol. During the cyclisation step the N-benzoyl-protecting group is cleaved. After partial work-up, crude indoline is reacted with acetic anhydride or a similar acetylating agent to protect the 1-nitrogen atom of the system.

Reaction (c) involves an aldol condensation similar to that of reaction (b) to provide the indoline cyclic structure but the 1-nitrogen atom is not protected in this stage. Instead the indole fragment is formed by aromatisation with active manganese dioxide or any other suitable dehydrogenating agent using an organic solvent such as acetone.

Reactions (d), (e) and (p) can be accomplished in two ways. The first of these methods involves the well-known Schmidt reaction in which the ketone is reacted with hydrazoic acid in the presence of a suitable acid such as sulphuric acid. Alternatively, the ketone can be converted to the corresponding oxime which is then subjected to the Beckmann rearrangement.

Reactions (f), (i) and (q) involve the sequential deprotection of the 1-nitrogen atom using a strong base such as potassium hydroxide followed by aromatisation using similar conditions to those specified for reaction (c) above.

The N-alkylation reactions (g) and (r) can be effected by generating the anion with a strong base such as sodium hydride at a temperature of 60° to 65° C. followed by alkylation with any suitable alkylating agent. The reaction (l) is carried out at a slightly higher temperature, for example from 70° to 75° C. and for a period of about three hours.

Reactions (h), (j) and (s) involve the reduction of the amide utilising a chemical reducing agent, for example sodium dihydrido bis(2-methoxy-ethoxy)aluminate or lithium aluminium hydride in an inert solvent such as benzene, toluene or tetrahydrofuran at a temperature of from, for example, 0° C. to 50° C.

Reaction (k) involves a conventional alkylation or acylating reaction which can be effected using reagents such as the acid chloride or anhydride or an appropriate alkyl halide or tosylate. The order of reactions (h) and (k) may be reversed.

Reaction (n) involves the reduction of the ketone of formula (II) by catalytic hydrogenation using hydrogen in the presence of Adam's catalyst and reaction (m) is carried out by the same procedure.

The reaction (o) can be effected by any suitable oxidative procedure, using for instance Jones reagent or pyridinium chlorochromate.

In order to obtain the compounds of formula (I) in which X is halogen, the corresponding compound of formula (I) in which X is hydrogen is reacted with a halogenating agent preferably in an organic solvent. For example in the case of the chloro compounds, the appropriate compound is reacted with a suitable source of positive chlorine for example N-chlorosuccinimide, sulphuryl chloride or N-chlorobenzotriazole, preferably following the procedure described in U.S. Pat. No. 4,098,790. In the case of the bromo compounds, the appropriate starting material is reacted with a suitable source of positive bromine such as for example, N-bromosuccinimide, pyridinium bromide perbromide and especially phenyl trimethyl ammonium tribromide.

The amides of formula (VI) and (VII) are novel. Accordingly, in a second aspect of the invention there is provided a compound of formula (VIII):

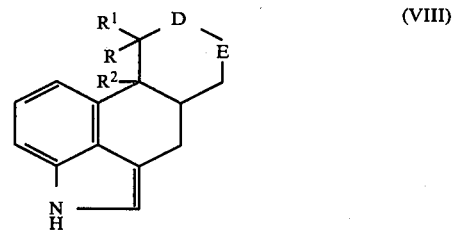

where the moiety D-E represents a group of formula:

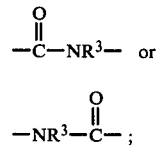

where R, $R^1$, $R^2$ and $R^3$ are as defined previously.

In a further aspect of the invention there is provided a method of preparing a compound of formula (I) which comprises (a) reducing a compound of formula (VIII), (b) in the case of compounds in which X is halogen, halogenating a compound of formula (I) in which X is hydrogen or (c) alkylating or acylating a compound of formula (I) in which $R^3$ is hydrogen.

The compounds of the invention have useful central nervous system activity.

They have low toxicity. This activity has been demonstrated in extensive testing in animal models using well-established procedures, such as the production of catalepsy, block of conditioned avoidance reponse and reversal of amphetamine-induced stereotyped behaviour in rats. Specifically, the compounds of formula (I) and pharmaceutically-acceptable acid addition salts thereof, are potent centrally acting compounds with neuroleptic, sedative or relaxant or anti-emetic properties. These properties, coupled with their high therapeutic index, render them useful in the treatment of mild anxiety states and certain kinds of psychotic conditions such as schizophrenia and acute mania.

The compounds of this invention are effective over a wide dosage range, the actual dose administered being dependent on such factors as the particular compound being used, the condition being treated and the type and size of mammal being treated. However, the dosage required will normally fall within the range of 0.05 to 10 mg./kg. per day, for example in the treatment of adult humans dosages of from 0.2 to 5 mg./kg. may be used.

The compounds and salts of the present invention will normally be administered orally or by injection and, for this purpose, said compounds and salts will usually be utilised in the form of a pharmaceutical composition. Such compositions are prepared in a manner well known in the pharmaceutical art and normally comprise at least one active compound or pharmaceutically-acceptable salt of the invention associated with a pharmaceutically-acceptable carrier therefor. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Some examples of suitable carriers are lactose, dextrose, sucrose, sorbitol, mannitol, starches, gum acacia, calcium phosphate, alginates, tragecanth, gelatin, syrup, methyl cellulose, methyl- and propyl-hydroxybenzoate, talc, magnesium stearate or mineral oil. The compositions of the invention may, as is well-known in the art, be formulated so as to provide quick, sustained or delayed release of the active ingredient after administration to the patient.

Depending on the route of administration, the foregoing compositions may be formulated as tablets, capsules or suspensions for oral use and injection solutions for parenteral use. Preferably the compositions are formulated in a dosage unit form, each dosage containing from 1 to 200 mg. more usually 5 to 100 mg., of the active ingredient.

The following non-limitative Examples will further illustrate the invention.

EXAMPLE 1

1-Benzoyl-4-acetonyl-1,2,2a,3-tetrahydrobenz[cd]indol-5(4H)-one

Methyllithium (1.3 M soln., 4 ml, 0.0052 m) in tetrahydrofuran (20 ml) distilled from lithium aluminiumhydride) was cooled to −25° C. Diisopropylamine (0.8 ml, 0.006 m) was added and stirred until gas evolution ceased. The solution was cooled to −70° C. and 1-benzoyl-1,2,2a,3-tetrahydrobenz[cd]indol-5(4H)-one (1.4 g, 0.004 m) added in one portion, warmed to −20° C. and stirred until a clear brown solution formed (45 minutes). Cooled to −70° C. and 2-nitropropene (0.5 g, 0.006 m) added dropwise, warmed to −30° C. and stirred for two hours. Perchloric acid (1 ml) was added and the reaction mixture stirred for 18 hours. The reaction mixture was then poured into water (100 ml), extracted into ethyl acetate, washed with water, dried (MgSO$_4$) and evaporated to dryness. Chromatography on Sorbsil U 30 silica gel (50% EtoAc/hexane) and crystallisation from methanol gave the title compound, yield 0.6 g (45%), m.p. 117°–119° C.

EXAMPLE 2

1-Benzoyl-4-(2-oxobutyl)-1,2,2a,3-tetrahydrobenz[cd]indol-5(4H)-one was similarly prepared from 1-benzoyl-1,2,2a,3-tetrahydrobenz[cd]indol-5(4H)-one and 2-nitrobutene as an non-crystallisable oil, 66% yield, b.p. 120° C./0.05 mm. Kugelrohr.

EXAMPLE 3

1-Benzoyl-4-(2-oxopentyl)-1,2,2a,3-tetrahydrobenz[cd]indol-5(4H)-one was prepared in a similar way to that described in Example 2. It was an oil,

EXAMPLE 4

1-Acetyl-2,3,4,5-tetrahydro-1H-indolo[3,4-fg]indan-7(6H)-one

1-Benzoyl-4-acetonyl-1,2,2a,3-tetrahydrobenz[cd]indol-5(4H)-one (1.3 g, 0.004 m) in ethanol (100 ml) under a nitrogen atmosphere was treated with potassium hydroxide (2.0 g) and refluxed for 2 hours. The reaction mixture was poured onto ice/water, extracted with chloroform and dried (MgSO$_4$). Acetic anhydride (1 ml) was added to the dried extracts and stirred for 1 hour. Evaporation to dryness and crystallisation from ethyl acetate/hexane gave the title product, yield 0.6 g (64%) m.p. 180°–182° C.

EXAMPLE 5

1-Acetyl-8-methyl-2,3,4,5-tetrahydro-1H-indolo[3,4-fg]indan-7(6H)-one was similarly prepared from 1-benzoyl-4-(2-oxobutyl)-1,2,2a,3-tetrahydrofuran[cd]indol-5(6H)-one, yield 57%, m.p. 223°–5° C.

EXAMPLE 6

1-Acetyl-6-ethyl-2,3,4,5-tetrahydro-1H-indolo[3,4-fg]indan-7(6H)-one was similarly prepared from 1-benzoyl-4-(2-oxopentyl)-1,2,2a,3-tetrahydrobenz[cd]-indol-5(6H)-one, yield 38% m.p. 168°–9° C.

EXAMPLE 7

1-Acetyl-2,3,4,5-tetrahydro-1H-indolo[3,4-fg]indan-7(6H)-one oxime

1-Acetyl-2,3,4,5-tetrahydro-1H-indolo[3,4-fg]indan-7(6H)-one (200 mg), hydroxylamine hydrochloride (100 mg) and sodium acetate (50 mg) in methanol (10 ml) were refluxed for 2 hours. The reaction mixture was allowed to cool, the title product recovered by filtration and washed with water, yield 200 mg. (95%). Structure confirmation was effected by NMR and mass spectral data.

EXAMPLE 8

1-Acetyl-8-methyl-2,3,4,5-tetrahydro-1H-indolo[3,4-fg]indan-7(6H)-one oxime was similarly prepared from -acetyl-8-methyl-2,3,4,5-tetrahydro-1H-indolo[3,4-fg]indan-7(6H)-one, yield 95%, m.p. >320° C. (dec).

EXAMPLE 9

1-Acetyl-1,2,3,4,5,6-hexahydroiondolo[4,3-fg]isoquinolin-8(7H)-one

1-Acetyl-2,3,4,5-tetrahydro-1H-indolo[3,4-fg]indan-7(6)-one oxime (200 mg) in polyphosphoric acid (2 ml) was stirred and heated to 60° C. for 2 hours. The reaction mixture was diluted with cold water, extracted with chloroform, washed with water, dried (MgSO$_4$) and evaporated to dryness. Crystallisation from methanol gave the title product, yield 160 mg (90%), m.p. 300°–5° C. (dec.).

EXAMPLE 10

1-Acetyl-9-methyl-1,2,3,4,5,6-hexahydroindolo[4,3-fg]isoquinolin-8(7H)-one was similarly prepared from 1-acetyl-8-methyl-2,3,4,5-tetrahydro-1H-indolo[3,4-fg]indan-7(6H)-one oxime, yield 180 mg (90%) m.p. 214°-6° C.

EXAMPLE 11

1-Acetyl-1,2,3,4,5,6-hexahydroindolo[4,3-fg]isoquinolin-8(7H)-one

1-Acetyl-2,3,4,5-tetrahydro-1H-indolo[3,4-fg]indan-7(6H)-one (2.2 g, 0.0087 m) in glacial acetic acid (20 ml) was stirred and warmed to 60° C. Sodium azide (0.6 g, 0.0087 m) was added followed by concentrated sulphuric acid (2 ml) dropwise over 5 minutes. The reaction mixture was stirred at 60°-65° C. until effervescence ceased. Two further additions of sodium azide and concentrated sulphuric acid were made to complete the conversion of all starting material. The reaction mixture was then poured onto a mixture of ice/saturated sodium bicarbonate solution, extracted into chloroform, washed with water, dried ($MgSO_4$) and evaporated to dryness. Crystallisation from methanol gave the title product, yield 1.7 g (73%) m.p. 300°-5° C. (dec.).

EXAMPLE 12

1-Acetyl-9-methyl-1,2,3,4,5,6-hexahydroindolo[4,3-fg]isoquinolin-8(7H)-one was similarly prepared from 1-acetyl-8-methyl-2,3,4,5-tetrahydro-1H-indolo[3,4-fg]indan-7(6H)-one (75%) m.p. 214°-6° C.

EXAMPLE 13

1-Acetyl-9-ethyl-1,2,3,4,5,6-hexahydroindolo[4,3-fg]isoquinoline-8(7H)-one was similarly prepared from 1-acetyl-8-ethyl-2,3,4,5-tetrahydro-1H-indolo[3,4-fg]indan-7(6H)-one (85%) m.p. 213°-215° C.

EXAMPLE 14

1-Acetyl-7-methyl-1,2,3,4,5,6-hexahydroindolo[4,3-fg]isoquinoline-8(7H)-one

1-Acetyl-1,2,3,4,5,6-hexahydroindolo[4,3-fg]isoquinolin-8(7H)-one (140 mg, 0.0005 m) was added to a stirred suspension of sodium hydride (50% dispersion, 30 mg, 0.0006 m) in dimethylformamide (10 ml) at 60° C. The reaction mixture was stirred for 30 minutes, cooled to 10° C. and methyl iodide (100 mg, 0.0007 m) added. Stirring was continued for a further 30 minutes, the reaction mixture diluted with water, extracted with chloroform, washed with water, dried ($MgSO_4$) and evaporated to dryness. The title product was crystallised from ethyl acetate, yield 60 mg, (37%) and its structure was confirmed by mass spectral evidence.

EXAMPLE 15

1-Acetyl-7,9-dimethyl-1,2,3,4,5,6-hexahydroindolo[4,3-fg]isoquinolin-8(7H)-one was similarly prepared from 1-acetyl-9-methyl-1,2,3,4,5,6-hexahydroindolo[4,3-fg]isoquinolin-8(7H)-one, (75%) m.p. 210°-212° C.

EXAMPLE 16

1-Acetyl-7-methyl-1,2,3,4,5,6-hexahydroindolo[4,3-fg]isoquinoline-8(7H)-one

1-Acetyl-1,2,3,4,5,6-hexahydroindolo[4,3-fg]isoquinolin-8(7H)one (2.7 g, 0.01 m) and cetyl trimethylammonium bromide (3.7 g, 0.01 m) suspended in tetrahydrofuran (50 ml) and stirred at room temperature. Methyl iodide (3.0 g, 0.02 m) and 50% sodium hydroxide (50 ml) were added and the mixture stirred vigorously for 18 hours. The reaction was poured into ice water, extracted with ethyl acetate, washed with water, dried ($MgSO_4$) and evaporated to dryness. Chromatography on U30 silica gel by elution with 1% methanol in chloroform and crystallisation from ethyl acetate gave the title compound 1.3 g (48%) m.p. 250°-255° C.

EXAMPLE 17

1-Acetyl-7,9-dimethyl-1,2,3,4,5,6-hexahydroindolo[4,3-fg]isoquinoline-8(7H)-one was similarly prepared from 1-acetyl-9-methyl-1,2,3,4,5,6-hexahydroindole[4,3-fg]isoquinoline-8(7H)-one, (58%) m.p. 210°-212° C.

EXAMPLE 18

1-Acetyl-9-ethyl-7-methyl-1,2,3,4,5,6-hexahydroindolo[4,3-fg]isoquinoline-8(7H)-one was similarly prepared from 1-acetyl-9-ethyl-1,2,3,4,5,6-hexahydroindole[4,3-fg]isoquinolin-8(7H)-one (61%) m.p. 179°-80° C.

EXAMPLE 19

1-Acetyl-9-methyl-7-n-propyl-1,2,3,4,5,6-hexahydroindolo[4,3-fg]isoquinolin-8(7H)-one was similarly prepared from 1-acetyl-9-methyl-1,2,3,4,5,6-hexahydroindolo[4,3-fg]isoquinolin-8(7H)-one (91%) m.p. 75°-78° C.

EXAMPLE 20

1-Acetyl-7-n-hexyl-9-methyl-1,2,3,4,5,6-hexahydroindolo[4,3-fg]isoquinolin-8(7H)-one was similarly prepared from 1-acetyl-9-methyl-1,2,3,4,5,6-hexahydroindolo[4,3-fg]isoquinolin-8(7H)-one (81%) m.p. 82°-84° C.

EXAMPLE 21

1-Acetyl-7-allyl-9-methyl-1,2,3,4,5,6-hexahydroindolo[4,3-fg]isoquinolin-8(7H)-one was similarly prepared from 1-acetyl-9-methyl-1,2,3,4,5,6-hexahydroindolo[4,3-fg]isoquinolin-8(7H)-one (94%) m.p. 135° C.

EXAMPLE 22

1-Acetyl-7-(3,3-dimethylpropen-2-yl)-9-methyl-1,2,3,4,5,6-hexahydroindolo[4,3-fg]isoquinolin-8(7H)-one was similarly prepared from 1-acetyl-9-methyl-1,2,3,4,5,6-hexahydroindolo[4,3-fg]isoquinolin-8(7H)-one (71%) m.p. 89°-90° C.

EXAMPLE 23

1-Acetyl-7-cyclopropylmethyl-9-methyl-1,2,3,4,5,6-hexahydroindolo[4,3-fg]isoquinolin-8(7H)-one was similarly prepared from 1-acetyl-9-methyl-1,2,3,4,5,6-hexahydroindolo[4,3-fg]isoquinolin-8(7H)-one. (42%) m.p. 177°-80° C.

EXAMPLE 24

1-Acetyl-7-benzyl-1,2,3,4,5,6-hexahydroindolo[4,3-fg]isoquinolin-8(7H)-one was similarly prepared from 1-acetyl-1,2,3,4,5,6-hexahydroindolo[4,3-fg]isoquinolin-8(7H)one (39%) m.p. 215°-218° C.

EXAMPLE 25

1-Acetyl-7,9-dimethyl-1,2,3,4,9,10-hexahydroindolo[4,3-fg]isoquinoline-8(7H)-one was prepared as in Example 14 except that the reaction mixture was stirred at 75° C. for 3 hours m.p. 233°–235° C.

EXAMPLE 26

1-Acetyl-7,9-dimethyl-1,2,3,4,5,6,9,10-octahydroindolo[4,3-fg]isoquinolin-8(7H)-one 1-Acetyl-7,9-dimethyl-1,2,3,4,9,10-hexahydroindolo[4,3-fg]isoquinolin-8(7H)-one (100 mg.) in ethanol (20 ml) was hydrogenated at 60 p.s.i. over platinum oxide (10 mg) for 4 hours. The catalyst was removed by filtration and the solvent removed in vacuo. Crystallisation from acetonitrile-diethyl ether gave the title compound m.p. 204°–206° C.

EXAMPLE 27

7-Methyl-1,4,5,6-tetrahydroindolo[4,3-fg]isoquinolin-8(7H)-one

1-Acetyl-7-methyl-1,2,3,4,5,6-hexahydroindolo[4,3-fg]isoquinolin-8(7H)-one (100 mg) in ethanol (20 ml) was treated with 50% NaOH solution (5 ml) and stirred at 60° C. for 18 hours. The reaction mixture was poured onto ice-water, extracted into chloroform, washed with water, dried (MgSO$_4$) and evaporated to dryness. The crude 7-methyl-1,2,3,4,5,6-hexahydroindolo[4,3-fg]isoquinolin 8(7H)-one was dissolved in acetone and stirred for 18 hours with manganese dioxide on activated carbon (1 g) [*Journal of Organic Chemistry*, 35, 3971 (1970)]. The manganese dioxide was removed by filtration and the solution evaporated to dryness. Crystallisation from ethyl acetate gave the title product as a crystalline product the structure of which was confirmed by mass spectral evidence.

EXAMPLE 28

7,9-Dimethyl-1,4,5,6-tetrahydroindolo[4,3-fg]isoquinolin-8(7H)-one was similarly prepared from 1-acetyl-7,9-dimethyl-1,2,3,4,5,6-hexahydroindolo[4,3-fg]isoquinolin-8(7H)-one, m.p. 237°–9° C.

EXAMPLE 29

9-Ethyl-7-methyl-1,4,5,6-tetrahydroindolo[4,3-fg]isoquinolin-8(7H)-one was similarly prepared from 1-acetyl-9-ethyl-7-methyl-1,2,3,4,5,6-hexahydroindolo[4,3 fg]isoquinolin-8(7H)-one (53%) m.p. 246°–9° C.

EXAMPLE 30

9-Methyl-7-n-propyl-1,4,5,6-tetrahydroindolo[4,3-fg]isoquinoline-8(7H)-one was similarly prepared from 1-acetyl-9-methyl-7-n-propyl-1,2,3,4,5,6-hexahydroindolo[4,3-fg]isoquinolin-8(7H)-one (36%)m.p. 192°–195° C.

EXAMPLE 31

7-n-Hexyl-9-methyl-1,4,5,6-tetrahydroindolo[4,3-fg]isoquinolin-8(7H)-one was similarly prepared from 1-acetyl-7-n-hexyl-9-methyl-1,2,3,4,5,6-hexahydroindolo[4,3-fg]isoquibolin-8(7H)-one (35%) m.p. 139°–141° C.

EXAMPLE 32

7-Allyl-9-methyl-1,4,5,6-tetrahydrindolo[4,3-fg]isoquinolin-8(7H)-one was similarly prepared from 1-acetyl-7-allyl-9-methyl-1,2,3,4,5,6-hexahydroindolo[4,3-fg]isoquinoline-8(7H)-one (55%).

EXAMPLE 33

7-(3,3-Dimethylpropen-2-yl)-9-methyl-1,4,5,6-tetrahydroindolo[4,3-fg]isoquinolin-8(7H)-one was similarly prepared from 1-acetyl-7-(3,3-dimethylpropen-2-yl)-9-methyl-1,2,3,4,5,6-hexahydroindolo[4,3-fg]isoquinolin-8(7H)-one (48%) m.p. 225°–30° C.

EXAMPLE 34

7-Cyclopropylmethyl-9ethyl-1,4,5,6-tetrahydroindolo[4,3-fg]isoquinolin-8(7H)-one was similarly prepared from 1-acetyl-7-cyclopropylmethyl-9-ethyl-1,2,3,4,5,6-hexahydroindolo[4,3-fg]isoquinolin-8(7)-one mp. 213°–215° C.

EXAMPLE 35

7-Benzyl-1,4,5,6-tetrahydroindolo[4,3-fg]isoquinolin-8(7H)-one was similarly prepared from 1-acetyl-7-benzyl-1,2,3,4,5,6-hexahydroindolo[4,3-g]isoquinolin-8(7H)-one (47%) m.p. 207°–208° C.

EXAMPLE 36

7,9-Dimethyl-1,4,5,6,9,10-hexahydroindolo[4,3-fg]isoquinolin-8(7H-one was similarly prepared from 1-acetyl-7,9-dimethyl-1,2,3,4,5,6,10-octahydroindolo[4,3-fg]isoquinolin-8(7H)-one m.p. 217°–219° C.

EXAMPLE 37

7-Methyl-1,4,5,6,7,8-hexahydroindolo[4,3-fg]isoquinoline maleate

7-Methyl-1,4,5,6-tetrahydroindolo[4,3-fg]isoquinolin-8(7H)-one (200 mg) was dissolved in dry benzene (10 ml) and stirred at room temperature. Sodium bis(2-methoxy-ethoxy)aluminum (Red-Al) (70% solution in benzene, 0.5 ml) was added and the mixture stirred for 2 hours. The reaction mixture was diluted with a cold water, extracted into ethyl acetate, washed and dried (Mg SO4). Maleic acid (0.1 g) in ethyl acetate (5 ml) was added and the salt allowed to crystallise, yield 220 mg (79%) m.p. 200°–202° C.

EXAMPLE 38

7,9-Dimethyl-1,4,5,6,7,8-hexahydroindolo[4,3-fg]isoquinoline was similarly prepared from 7,9-dimethyl-1,4,5,6-tetrahydroindolo[4,3-fg]isoquinolin-8(7H)-one and similarly characterised, m.p. 166°–169° C.

EXAMPLE 39

9-Ethyl-7-methyl-1,4,5,6,7,8-hexahydroindolo[4,3-fg]isoquinoline maleate was similarly prepared from 9-ethyl-7-methyl-1,4,5,6-tetrahydroindolo[4,3-fg]isoquinolin-8(7H)-one (80%) m.p. 175°–177°.

EXAMPLE 40

9-Methyl-7-n-propyl-1,4,5,6,7,8-hexahydroindolo[4,3-fg]isoquinoline maleate was similarly prepared from 9-methyl-7-n-propyl-1,4,5,6-tetrahydroindolo[4,3-fg]isoquinolin-8(7H)-one (76%) m.p. 130°–132° C.

EXAMPLE 41

7-n-Hexyl-9-methyl-1,4,5,6,7,8-hexahydroindolo[4,3-fg]isoquinoline maleate was similarly prepared from 7-n-hexyl-9-methyl-1,4,5,6-tetrahydroindolo[4,3-fg]isoquinoline-8(7H)-one (75%) m.p. 149°–151° C.

EXAMPLE 42

7-Allyl-9-metyl-1,4,5,6,7,8-hexahydroindolo[4,3-fg]isoquinolin moleate was similarly prepared from 7-allyl-9-methyl-1,4,5,6-tetrahydroindolo[4,3-fg]isoquinolin-8(7H)-one (80%) m.p. 153°–155° C.

EXAMPLE 43

7-(3,3-Dimethylpropen-2yl)-9-methyl-1,4,5,6,7,8-hexahydroindolo[4,3-fg]isoquinoline maleate was similarly prepared from 7-(3,3-dimethylpropen-2-yl)-9-methyl-1,4,5,6-tetrahydroindolo[4,3-fg]isoquinoline-8(7H)-one (80%) m.p. 105°–6°.

EXAMPLE 44

7-Cyclopropylmethyl-9-ethyl-1,4,5,6,7,8-hexahydroindolo[4,3-fg]isoquinoline maleate was similarly prepared from 7-cyclopropylmethyl-9-ethyl-1,4,5,6-tetrahydroindolo[4,3-fg]isoquinolin-8(7H)-one.

EXAMPLE 45

7-Benzyl-1,4,5,6,7,8-hexahydroindolo[4,3-fg]isoquinoline maleate was similarly prepared from 7-benzyl-1,4,5,6-tetrahydroindole[4,3-fg]isoquinolin-8(7H)-one (61%) m.p. 206°–208° C.

EXAMPLE 46

7,9-Dimethyl-1,4,5,6,7,8,9,10-octahydroindolo[4,3-fg]isoquinoline maleate was similarly prepared from 7,9-dimethyl-1,4,5,6,9,10-hexahydroindolo[4,3-fg]isoquinoline 8(7H)-one.

EXAMPLE 47

1,4,5,6-Tetrahydroindolo[4,3-fg]isoquinolin-8(7H)-one

1-Acetyl-1,2,3,4,5,6-hexahydroindolo[4,3-fg]isoquinoline-8(7H)-one (100 mg) in ethanol (5 ml) and dioxan (5 ml) was treated with 50% sodium hydroxide solution (5 ml) and stirred for 18 hours. The reaction mixture was poured into ice-water, extracted into chloroform, washed with water, dried (MgSO$_4$) and evaporated to dryness. The crude 1,2,3,4,5,6-hexahydroindolo[4,3-fg]isoquinolin-8(7H)-one was dissolved in acetone and stirred for 18 hours with manganese dioxide on activated carbon (1 g). The manganese dioxide was removed by filtration and the solution evaporated to dryness. Crystallisation from ethyl acetate gave the title product. m.p. 142°–144° C. The structure was confirmed by a combination of infra-red, ultra-violet and mass spectral data.

EXAMPLE 48

9-Methyl-1,4,5,6-tetrahydroindolo[4,3-fg]isoquinolin-8(7H)-one was similarly prepared from 1-acetyl-9-methyl-1,2,3,4,5,6-hexadhydroindolo[4,3-fg]isoquinolin-8(7H)-one, m.p. 198° C. (ethyl acetate).

EXAMPLE 49

7-Cyclopropylacetamido-9-methyl-1,4,5,6-tetrahydroindolo[4,3-fg]isoquinolin-8(7H)-one.

To a solution of 9-methyl-1,4,5,6-tetrahydroindolo[4,3-fg]isoquinoline-8(7H)-one (40 mg) in methylene chloride (10 ml) was added triethylamine (5 drops) and cyclopropane carboxylic acid chloride (4 drops). The reaction was stirred for 4 hours diluted with more methylene chloride, washed with water, dried (MgSO$_4$) and evaporated to dryness. Crystallisation from ethyl acetate gave the title compound.

EXAMPLE 50

1,4,5,6,7,8-Hexahydroindolo[4,3-fg]isoquinoline 1,4,5,6-Tetrahydroindolo[4,3-fg]isoquinolin-8(7H)-one (20 mg) was dissolved in dry benzene (10 ml) and stirred at room temperature. Red-Al (70% solution in benzene, 0.1 ml) was added and stirred for 2 hours. The reaction mixture was diluted with water, extracted into chloroform, washed with water, dried (MgSO$_4$) and evaporated to dryness. The crude amide was dissolved in ethyl acetate (5 ml) and maleic acid 10 (mg) in ethyl acetate (1 ml) added. The crystals of product were collected by filtration.

EXAMPLE 51

9-Methyl-1,4,5,6,7,8-hexahydroindolo[4,3-fg]isoquinoline maleate was similarly prepared from 9-methyl-1,4,5,6-tetrahydroindolo[4,3-fg]isoquinoline-8(7H)-one, m.p. 198°–200° C.

EXAMPLE 52

7-Cyclopropylmethyl-9-methyl-1,4,5,6,7,8-hexahydroindolo[4,3-fg]isoquinoline maleate was similarly prepared from 7-cyclopropylacetamido-9-methyl-1,4,5,6-tetrahydroindolo[4,3-fg]isoquinolin-8(7H)-one.

EXAMPLE 53

4,5-Dihydro-1H-indolo[3,4-fg]indan-7(6H)-one

1-Benzoyl-4-acetonyl-1,2,3,4-tetrahydrobenz[cd]indol-5(4H)-one (1.3 g, 0.004 m) in ethanol (100 ml) under a nitrogen atmosphere was treated with potassium hydroxide (2.0 g) and refluxed for 2 hours. The reaction mixture was poured onto ice/water, extracted into chloroform, dried (MgSO$_4$) and evaporated to dryness. The crude 2,3,4,5-tetrahydro-1H-indolo[4,3-ef]indan-7(6H)-one was dissolved in acetone (50 ml) and stirred with manganese dioxide on activated charcoal for 36 hours. The manganese dioxide was removed by filtration and the solution evaporated to dryness. Crystallisation from chloroform/ethyl acetate gave the title product as a crystalline solid.

EXAMPLE 54

8-Methyl-4,5-dihydro-1H-indolo[3,4-fg]indan-7(6H)-one was similarly prepared from 1-benzoyl-4-(2-oxobutyl)-1,2,2a,3,tetrahydrobenz([cd]indol-5(4H)-one, 30% m.p. 257°–9° C.

EXAMPLE 55

4,5-Dihydro-1H-indolo[3,4-fg]indan-7-(6H)-one oxime 4,5-Dihydro-1H-indolo[3,4-fg]indan-7(6H)-one (200 mg), hydroxyalamine hydrochloride (100 mg) and sodium acetate (50 mg) in n-propanol (10 ml) was refluxed for 18 hours. The reaction mixture was diluted with chloroform, filtered through a pad of alumina and evaporated to dryness. Crystallisation from carbon tetrachloride gave the title product, yield 150 mg (75%).

EXAMPLE 56

8-Methyl-4,5-dihydro-1H-indolo[3,4-fg]indan-7(6H)-one oxime was similarly prepared from 8-methyl-4,5-dihydro-1H-indolo[3,4-fg]indan-7(6H)-one m.p. 190°–200° C.

EXAMPLE 57

1-Acetyl-7-hydroxy-8-methyl-2,3,4,5,6,7,8,9-octahydro-1H-indolo[3,4-fg]indane

1-Acetyl-8-methyl-2,3,4,5-tetrahydro-1H-indolo[3,4-fg]indan-7(6H)-one (100 mg) in ethanol (100 ml) with platinum oxide (10 mg) was hydrogenated at 60 p.s.i. until hydrogen uptake ceased. The catalyst was removed by filtration and the solution evaporated to dryness. Crystallisation from ethanol gave the title product, yield 80 mg (80%) m.p. 223°-4° C.

EXAMPLE 58

1-Acetyl-8-methyl-2,3,4,5,8,9-hexahydro-1H-indolo[3,4-fg]indan-7(6H)-one

1-Acetyl-7-hydroxy-8-methyl-2,3,4,5,6,7,8,9-octahydro-1H-indolo[3,4-fg]indane (50 mg) in acetone (10 ml) was stirred and treated with Jones reagent (1 ml). The stirring was continued for 18 hours and then excess methanol was added to destroy excess reagent. The reaction mixture was then evaporated to dryness and partitioned between water and chloroform, solvent separated, washed with water, dried (MgSO$_4$) and evaporated to dryness to yield the title product. The product was crystallised from ethyl acetate (68%) m.p. 171°-172° C.

EXAMPLE 59

1-Acetyl-9-methyl-1,2,3,4,5,6,9,10-octahydroindolo[3,4-gh]isoquinolin-7(8H)-one

1-Acetyl-8-methyl-2,3,4,5,8,9-hexahydro-1H-indolo[3,4-fg]indan-7(6H)-one (100 mg) in glacial acetic acid (5 ml) was stirred and warmed to 50° C. Sodium azide (40 mg) was then added followed by concentrated sulphuric acid (0.1 ml). Stirring continued at 50°-55° C. until gas evolution ceased. A further addition of sodium azide and concentrated sulphuric acid ensured complete conversion of starting material. The reaction was poured onto ice/saturated sodium bicarbonate solution, extracted into chloroform, washed with water, dried (MgSO$_4$) and evaporated to dryness. Crystallisation from ethyl acetate gave the title product, m.p. 224°-226° C.

EXAMPLE 60

9-Methyl-1,4,5,6,9,10-hexahydroindolo[3,4-gh]isoquinolin-7(8H)-one

1-Acetyl-9-metyl-1,2,3,4,5,6,9,10-octahydroindolo[3,4-gh]isoquinolin-7(8H)-one (100 mg) in ethanol (10 ml) was stirred at room temperature. 50% NaOH solution (5 ml) was added to the stirred mixture and stirring continued for 18 hours. The reaction mixture was then poured onto ice water, extracted into chloroform, washed with water, dried (MgSO$_4$) and evaporated to dryness to yield the title product, the structure of which was confirmed by NMR and mass spectral data.

EXAMPLE 61

1-Acetyl-8,9-dimethyl-1,2,3,4,5,6,9,10-octahydroindolo[3,4-gh]isoquinolin-7(8H)-one A solution of 1-acetyl-9-methyl-1,2,3,4,5,6,9,10-octahydroindolo3,4-gh]isoquinolin-7(8H)one (100 mg) and sodium hydride (20 mg) in dry dimethylformamide (20 ml) was stirred in a nitrogen atmosphere and warmed to 60° C. for 30 minutes. The reaction was cooled to 10° C. and methyl iodide (0.1 ml) added. The reaction was stirred for 30 minutes and diluted with water. Extraction with chloroform, washing with water, drying (MgSO4) and evaporation to dryness gave the title compound which was crystallised from ethyl acetate m.p. 184°-186° C.

EXAMPLE 62

8,9-Dimethyl-1,4,5,6,9,10-hexahydroindolo[3,4-gh]isoquinolin-7(8H)-one

1-Acetyl-8,9-dimethyl-1,2,3,4,5,6,9,10-octahydroindolo[3,4-gh]isoquinolin-7(8H)-one (0.3 g) in acetic acid (10 ml) and concentrated hydrochloric acid (10 ml) was refluxed for 5 hours. The reactions mixture was poured into ice water, basefed with NaOH, extracted into chloroform, washed, dried (MgSO$_4$) and evaporated to dryness. The white solid was redissolved in acetone (20 ml) and MnO$_2$/C (3 g) added. The mixture was stirred for 10 hours and the catalyst filtered off, evaporation of the solvent in vacuo and crystallisation from ethyl acetate gave the title compound m.p. 250°-252° C.

EXAMPLE 63

8,9-Dimethyl-1,4,5,6,7,8,9,10-octahydroindolo[3,4-gh]isoquinoline 8,9-Dimethyl-1,4,5,6,9,10-hexahydroindolo[3,4-gh]isoquinolin-7(8H)-one (50 mg) dissolved in dry benzene (10 ml) was stirred at room temperature and "Red-Al" (0.1 ml) added. The solution was stirred for 2 hours, poured into cold water, extracted with chloroform, washed with water, dried (MgSO$_4$) and evaporated to dryness to yield the title product, the structure of which was confirmed by a combination of NMR and mass spectral data.

EXAMPLE 64

7,9-Dimethyl-1,4,5,6,7,8-hexahydroindolo[4,3-fg]isoquinoline (700 mg) was dissolved in THF (50 ml) and phenyl trimethylammonium tribromide (1.1 g) was added. The mixture was stirred for 2 hours at room temperature, diluted with water, made basic with sodium hydroxide solutions, extracted with ethyl acetate, washed, dried and evaporated to dryness. The crude product was chromatographed on basic alumina with chloroform to give, on evaporation, 500 mg of a white solid. This was dissolved in ethanol and maleic acid (0.3 g) was added. The solution was boiled with ether until crystals appeared. 2-Bromo-7,9-dimethyl-1,4,5,6,7,8-hexahydroindolo[4,3-fg]isoquinoline(maleate salt) was filtered off, m.p. 194°-196° C.

The following Examples illustrate pharmaceutical formulations containing the active compounds of the invention. The active ingredient used was 7,9-dimethyl-1,4,5,6,7,8-hexahydroindolo[4,3-fg]isoquinoline; however, it will be appreciated that this compound may be replaced by other active solid compounds of the invention.

EXAMPLE 65

Tablets each containing 10 mg of active ingredient were made up as follows:

| | |
|---|---|
| Active ingredient | 10 mg |
| Potato Starch | 45 mg |
| Lactose | 35 mg |
| Polyvinylpyrrolidone | 4 mg |
| (as 10% solution in | |

| | |
|---|---|
| water) | |
| Sodium starch glycolate | 4.5 mg |
| Magnesium Stearate | 0.5 mg |
| Talc | 1 mg |
| Total | 100 mg |

The active ingredient, starch and lactose were passed through a No. 44 mesh B.S. sieve and mixed thoroughly. The solution of polyvinylpyrrolidone was mixed with the resultant powders which were then passed through a No. 12 mesh B.S. sieve. The granules so produced were dried at 50°–60° C. and passed through a No. 16 mesh B.S. sieve. The sodium starch glycolate, magnesium stearate and talc, previously passed through a No. 60 mesh B.S. sieve, were then added to the granules which, after mixing, were compressed on a tablet machine to yield tablets each weighing 100 mg.

EXAMPLE 66

Capsules each containing 20 mg of medicament were made as follows:

| | |
|---|---|
| Active ingredient | 20 mg |
| Starch | 89 mg |
| Lactose | 89 mg |
| Magnesium Stearate | 2 mg |
| Total | 200 mg |

The active ingredient, lactose, starch and magnesium stearate were passed through a No. 44 mesh B.S. sieve and filled into hard gelatin capsules in 200 mg quantities.

EXAMPLE 67

Suppositories each containing 25 mg of active ingredient were made as follows:

| | |
|---|---|
| Medicament | 25 mg |
| Saturated fatty acid glycerides to | 2,000 mg |

The active ingredient was passed through a No. 60 mesh B.S. sieve and suspended in the saturated fatty acid glycerides previously melted using the minimum heat necessary. The mixture was then poured into a suppository mould of nominal 2 g capacity and allowed to cool.

EXAMPLE 68

Suspensions each containing 5 mg of medicament per 5 ml dose were made as follows:

| | |
|---|---|
| Medicament | 5 mg |
| Sodium carboxymethyl-cellulose 50 | 50 mg |
| Syrup | 1.25 ml |
| Benzoic Acid solution | 0.01 ml |
| Flavour | q.s. |
| Colour | q.s. |
| Chloroform water to | 5 ml |

The medicament was passed through a No. 44 mesh B.S. sieve and mixed with the sodium carboxymethylcellulose 50 and syrup to form a smooth paste. The benzoic acid solution, flavour and colour were diluted with some of the chloroform water and added, with constant stirring. Sufficient chloroform water was then added to produce the required volume.

We claim:

1. An isoquinoline compound of formula (I)

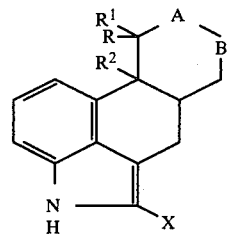

wherein the moiety A-B represents a group of formula:

$$-CH_2-NR^3- \text{ or } -NR^3-CH_2-;$$

wherein $R^3$ represents hydrogen, $C_{1-16}$ alkyl, $C_{3-6}$ cycloalkyl, $C_{3-6}$ cycloalkyl-$C_{1-4}$ alkyl, benzyl, benzyl substituted with from 1–3 of the following substituents: halogen, methyl, methoxy, nitro; $C_{3-6}$ alkenyl or $C_{1-4}$ alkanoyl;

wherein R represents hydrogen, $C_{1-6}$ alkyl, $C_{3-6}$ cycloalkyl, benzyl benzyl substituted with from 1–3 of the following substituents: halogen, methyl, methoxy, nitro;

wherein $R^1$ and $R^2$ each represent hydrogen or taken together represent a chemical bond only except that $R^1$ and $R^2$ represent hydrogen only when A-B is $-NR^3-CH_2-$; and wherein X is hydrogen or halogen; or an acid-addition salt thereof.

2. A compound according to claim 1 in which X is hydrogen.

3. A compound according to claim 1 in which X is chlorine or bromine.

4. A compound according to claim 1 in which A-B represents $-NR^3-CH_2-$ and $R^1$ and $R^2$ each represent hydrogen.

5. A compound according to claim 1 in which A-B represents $-CH_2-NR^3-$.

6. A compound according to claim 1 in which R and $R^3$ are $C_{1-4}$ alkyl.

7. A pharmaceutical formulation adapted for the treatment of mild anxiety states, schizophrenia and acute mania in unit dosage form comprising from 1–200 mg. per dosage unit of a compound for formula I as claimed in claim 1 or a pharmaceutically-acceptable salt thereof, associated with a pharmaceutically-acceptable carrier therefor.

8. A method of treating an animal susceptible to or suffering from a disorder of the central nervous system which comprises administering the said animal a chematherapeutically effective amount of a compound of formula (I) as claimed in claim 1, or a pharmaceutically-acceptable acid-addition salt thereof.

9. A method of treating a mammal, including a human, for a mild anxiety state, or for schizophrenia or acute mania by administering from 0.05–10 mg./kg./day of a compound of a compound of formula (I) according to claim 1 or a pharmaceutically-acceptable salt thereof.

* * * * *